(12) United States Patent
Lalgudi et al.

(10) Patent No.: US 11,724,981 B2
(45) Date of Patent: Aug. 15, 2023

(54) CATIONIC SURFACTANTS COMPRISING AN ETHER LINK

(71) Applicant: Battelle Memorial Institute, Columbus, OH (US)

(72) Inventors: Ramanathan S. Lalgudi, Westerville, OH (US); Robert J. Cain, Lewis Center, OH (US); Manoj Kumar Valluri, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 130 days.

(21) Appl. No.: 17/059,587

(22) PCT Filed: May 30, 2019

(86) PCT No.: PCT/US2019/034604
§ 371 (c)(1),
(2) Date: Nov. 30, 2020

(87) PCT Pub. No.: WO2019/232180
PCT Pub. Date: Dec. 5, 2019

(65) Prior Publication Data
US 2021/0139409 A1    May 13, 2021

Related U.S. Application Data

(60) Provisional application No. 62/677,965, filed on May 30, 2018.

(51) Int. Cl.
*C07C 213/06* (2006.01)
*C07C 217/58* (2006.01)
*C09K 8/584* (2006.01)

(52) U.S. Cl.
CPC .......... *C07C 213/06* (2013.01); *C07C 217/58* (2013.01); *C09K 8/584* (2013.01)

(58) Field of Classification Search
None
See application file for complete search history.

(56) References Cited

U.S. PATENT DOCUMENTS

| | | |
|---|---|---|
| 3,070,608 A | 12/1962 | Kuester et al. |
| 6,320,064 B1 | 11/2001 | Oftring et al. |
| 2006/0217284 A1 | 9/2006 | Hinrichs et al. |

FOREIGN PATENT DOCUMENTS

CA            731107 A      3/1966

OTHER PUBLICATIONS

Negin, Chegenizadeh et al., Most common surfactants employed in chemical enhanced oil recovery, Petroleum 3, (2017), 197-211.

(Continued)

*Primary Examiner* — Sudhakar Katakam
*Assistant Examiner* — Jennifer C Sawyer
(74) *Attorney, Agent, or Firm* — Greer, Burns & Crain, Ltd.

(57) ABSTRACT

A cationic surfactant and a method of making the cationic surfactant are described. The method comprises reacting a lipophilic bio-based material having at least one epoxy functional group and a hydrophilic organic compound having at least one cationic functional group and at least one hydroxyl functional group to form a reaction product containing a stable ether linkage connecting the lipophilic bio-based material to the organic compound. At least a portion of the cationic functional groups is neutralized or ion exchanged with an organic acid. Incorporation of the simple organic acid reduces the surfactant's aquatic toxicity and acts as a substrate to encourage co-digestion of the surfactant molecule, making the compound more biodegradable.

11 Claims, 1 Drawing Sheet

(56) References Cited

OTHER PUBLICATIONS

International Search report from corresponding PCT application No. PCT/US2019/034604, dated Jul. 29, 2019.
Written Opinion from corresponding PCT application No. PCT/US2019/034604, dated Jul. 29, 2019.
International Preliminary Report on Patentability for corresponding PCT application No. PCT/US2019/034604 dated Dec. 1, 2020.

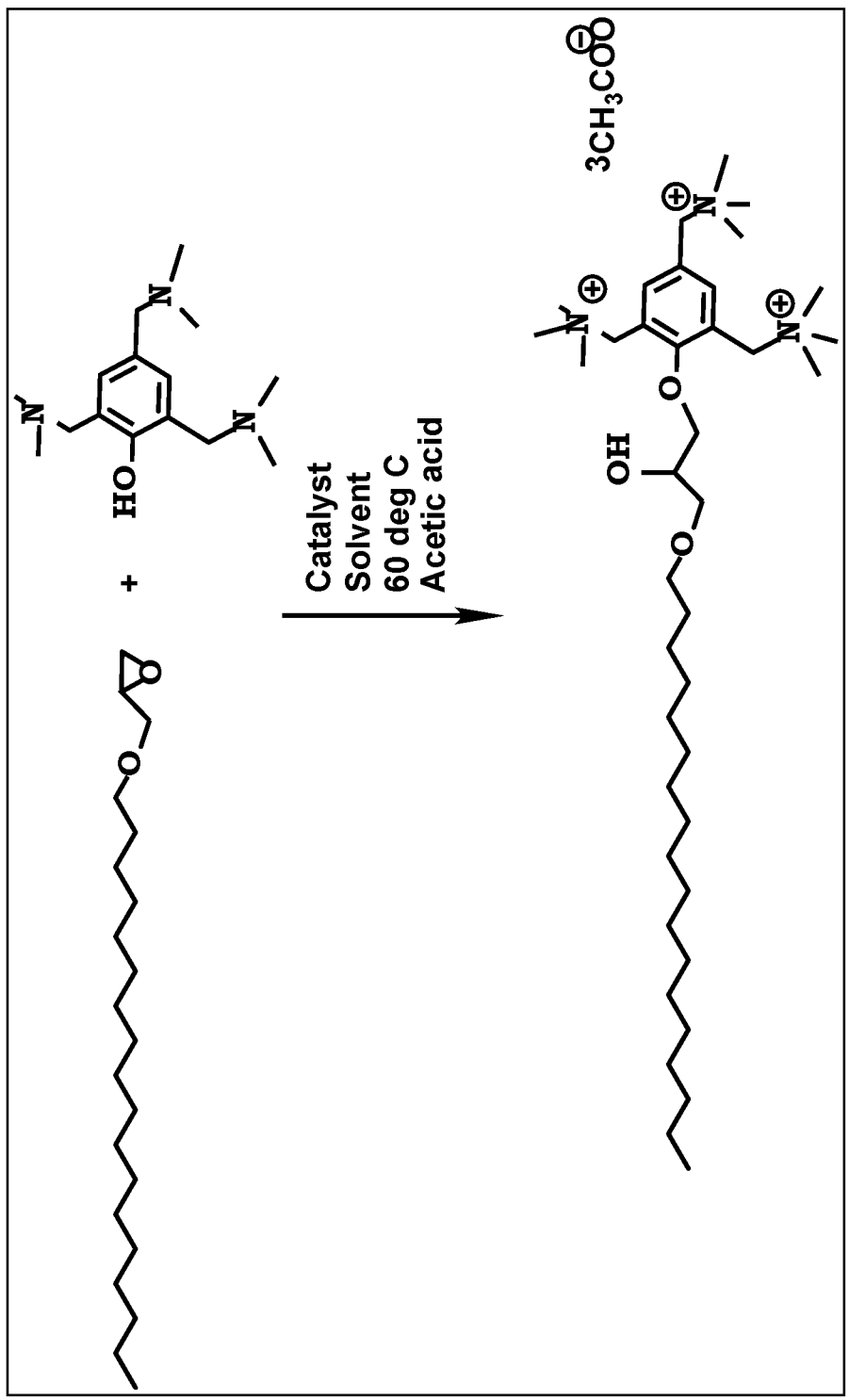

CATIONIC SURFACTANTS COMPRISING AN ETHER LINK

CROSS-REFERENCE TO RELATED APPLICATIONS

This application is a U.S. National Phase under 35 U.S.C.§ 371 of International Application No. PCT/US/2019/034604, filed May 30, 2019 which claims the benefit of U.S. Provisional Patent Application Ser. No. 62/677,965, filed May 30, 2018, entitled Cationic Surfactants, which are hereby incorporated by reference in their entirety.

BACKGROUND

The oilfield chemical market is extensive and will continue to grow as oil producers look for innovative and less expensive ways to drill and produce oil from depleted reservoirs. Though the oil price has been a limiting factor in the development of this market, a stable low-price environment such as the current one is likely to drive oilfield chemical companies to expand their portfolio and offerings to include more cost-effective and eco-friendly solutions to oilfield issues.

BRIEF DESCRIPTION OF THE DRAWINGS

The FIGURE is an illustration of one example of a reaction to form a cationic surfactant according to the present invention.

SUMMARY AND DETAILED DESCRIPTION

A cationic surfactant has been developed using lipophilic bio-based material having at least one epoxy functional group, such as epoxidized soybean oil. The cationic surfactant has a very stable ether linkage as opposed to less stable ester linkages.

A common challenge with cationic surfactants is their toxicity and resistance to biodegradation. For consumer applications, it is common to use esterquats, which use an ester bond to connect the quaternary ammonium functional group to the hydrocarbon backbone. The ester bond creates a weak point in the molecule where biodegradation can begin, allowing for good biodegradability of these compounds. However, esterquats are less useful in oil and gas applications where the high pressure, temperature, and pH extremes can cause chemical degradation of the surfactant before it can work effectively in the subsurface.

The current invention resolves the chemical instability by using an ether bond to join the cationic group to the lipophilic tail. In some embodiments, biodegradability is addressed by incorporating a simple organic acid as the counter-ion in the surfactant. Acetic acid, for example, is a common intermediate metabolic product from bacteria, and is readily biodegradable. The counter-ion serves as a substrate to promote biodegradation, leading to co-digestion of the more chemically stable balance of the surfactant. Co-digestion is a common phenomenon in water treatment, where introduction of a readily digestible substrate leads to biological destruction of normally recalcitrant organic compounds. In the case of the surfactant in discussion, the molecule is chemically stable due to its ether bond and holds up well in harsh chemical conditions, but is susceptible to biodegradation if it is released to surface waters or municipal treatment plants. This preserves its utility while reducing its environmental impact.

Co-digestion may also be achieved by introduction of readily biodegradable compounds into the surfactant product, not necessarily as a counter-ion. Incorporating the counterion for co-digestion may also work for existing cationic surfactants.

The cationic surfactant has been found to alter the rock-fluid behavior of the reservoir favorably towards improving oil recovery better compared to some of the industrial surfactants. It also provides flexibility in the ionic strength and length of the carbon chain to suit various oilfield chemistry needs. Because the cationic surfactant is made from natural oil derivatives, it is less expensive to formulate, and it has a secure supply chain. The cationic surfactant has application as an economical and eco-friendly solution for improving oil recovery from carbonate reservoirs. It has the potential to solve oil recovery and near-wellbore issues at a lower price to the operator and with less impact on the environment compared with the products currently in use.

The cationic surfactant is formed by reacting a lipophilic bio-based material having at least one epoxy functional group and a hydrophilic organic compound having at least one cationic functional group and at least one hydroxyl functional group. The reaction between the epoxy functional group and the hydroxyl functional group connects the lipophilic bio-based material to the hydrophilic organic compound via an ether linkage. Ether linkages are stable in acids and alkali as opposed to ester linkages which are not.

The FIGURE illustrates the production of a cationic surfactant according to the present invention. In this example, stearyl alcohol was reacted with epichlorohydrin, and the resulting epoxy functional bio-based material was reacted with 2,4,6-Tris dimethylaminomethyl phenol (DMP-30). The product obtained was neutralized with acetic acid to form the cationic surfactant octadecyl glycidyl ether.

The reaction can take place in the presence of a catalyst. Suitable catalysts include salts of tetrafluoroborate, including, but not limited to, comprises copper(II) tetrafluoroborate, cobalt (II) tetrafluoroborate, iron (II) tetrafluoroborate, zinc (II) tetrafluoroborate, nickel (II) tetrafluoroborate, and combinations thereof.

The reaction can take place in the presence of a solvent for the cationic surfactant because in some cases, the cationic is diluted for use. Suitable solvents include, but are not limited to, comprises acetone, methyl ethyl ketone, toluene, xylene, or combinations thereof, The reaction can be exothermic. Therefore, typical reaction conditions include a temperature in the range of 0° C. to 100° C., or 0° C. to 80° C., or 0° C. to 60° C. Reaction in a solvent may be beneficial to slow down the reaction kinetics.

In some situations, the reaction product is a surfactant, and no further reaction is needed to obtain the surfactant. In this case, the reaction product can optionally be contacted with an acid, for example an organic acid, to replace the counter-ion in the reaction product with the counter-ion in the acid. The acid may replace 50% to 100% of the counter-ions in the reaction, or more than 55%, or more than 60%, or more than 65%, or more than 70%, or more than 75%, or more than 80%, or more than 85%, or more than 90%, or more than 95%, or 80% to 95%. Suitable acids include, but are not limited to, acetic acid, formic acid, proprionic acid, butyric acid, malic acid, lactic acid, citric acid, or combinations thereof. In some cases, when the reaction product is a permanent cation, no further reaction is needed; however, optional ion exchange of cations may be performed if desired. Examples of cationic functional groups which are permanent cations include, but are not limited to, quaternary ammoniums, quaternary phosphoniums, and tertiary sulfoniums. The surfactant can then be separated from the solution. The separation may be accomplished using any suitable separation methods, including but not limited to, an ion exchange column.

In some situations, the cationic functional group of the reaction product should be neutralized in order to function as a surfactant. The cationic functional groups can be neutralized using carbon dioxide or a carboxylic acid, including, but not limited to, acetic acid, formic acid, proprionic acid, butyric acid, malic acid, lactic acid, citric acid, or combinations thereof. Typically more than 70 mol % of the cationic functional groups are neutralized, or more than 75 mol %, or more than 80 mol %, or more than 85 mol %, or more than 90 mol %, or more than 95 mol %, or 80 mol % to 100 mol %. In some cases when the reaction product is not a permanent cation, the reaction product may need to be neutralized. Examples of cationic functional groups which are not permanent cations include, but are not limited to, primary, secondary, and tertiary amines, primary, secondary, and tertiary phosphines, and guanidine derivatives with one or more organic groups bonded to the guanidine nitrogens.

Neutralization provides hydrophilic to lipophilic balance (HLB) and makes the molecule a surfactant. The HLB is typically in the range of 4 to 40, or in the range of 6 to 30, or in the range of 8 to 28. HLB is calculated as described in J T Davis, Gas/Liquid and Liquid/Liquid Interfaces. Proceedings of 2nd International Congress Surface Activity, Butterworths, London 1957, which calculation is incorporated herein by reference.

The resulting surfactant was tested for applicability as an oilfield chemical because it possesses at least one cationic functionality. Estrogenic and anti-estrogenic activity tests performed with the surfactant determined that the chemical is environmentally benign. Additionally, aquatic toxicity testing showed much reduced toxicity compared to typical cationic surfactants. The surfactant was also tested for its impact on rock-fluid behavior and the resultant oil recovery through spontaneous imbibition using actual reservoir rock and oil samples from Ohio's dolomitic reservoirs. The cationic surfactant favorably altered the rock-fluid behavior, which also improved oil recovery from aged core samples. A comparison of the surfactant's performance with two commercial products suggested improved recovery and a significant potential to provide a cost effective and environmentally friendly solution to some of the oil and gas industry's chemical problems.

By bio-based material, we mean materials that are derived from plants and other renewable agricultural, marine, and forestry materials and that provide an alternative to conventional petroleum derived products. (Ref: US Department of Agriculture, Biopreferred® Program).

Neutralization or ion exchange may improve the solubility of the cationic surfactant. In some cases, where the cationic functional group is a permanent cation, the counter ion of the cationic functional group can be ion exchanged with the counter ion in an acid, such as an organic acid. In some cases, where the cationic functional group is not a permanent cation, the cationic functional group can neutralized with an acid, such as an organic acid, or carbon dioxide. A permanent cation may have a pKa of 13 or above, and a cation which is not a permanent cation may have a pKa of less than 13, for example. A cation is an ion molecule (or even atom) with a fewer electrons than protons giving it a positive charge. Nitrogen containing molecules can gain or lose elemental $H^+$ ions, to gain a net electrical charge, such as, for example, primary, secondary, or tertiary amines. This can be accomplished with exposure to acids or bases, which can donate or accept protons. In this sense, primary, secondary, and tertiary amines can be exchangeable. Cationic or positive charge formation of an amine would require donation of a proton or be related to acid exposure. Quaternary ammonium cations are considered permanent or stable regardless of the pH of their solution.

One aspect of the invention is a method of making a cationic surfactant. In one embodiment, the method comprises reacting a lipophilic bio-based material having at least one epoxy functional group and a hydrophilic organic compound having a cationic functional group and at least one hydroxyl functional group to form a reaction product containing an ether linkage connecting the lipophilic bio-based material to the organic compound.

In some embodiments, the method further comprises neutralizing the cationic functional group in the reaction product; or ion exchanging the counter ion in the cationic functional group.

In some embodiments, the lipophilic bio-based material having at least one epoxy functional group comprises epoxidized soybean oil, epoxidized canola oil, epoxidized linseed oil, epoxidized high oleic soybean oil, epoxidized olive oil, epoxidized peanut oil, epoxidized palm oil, epoxidized hemp oil, epoxidized algal oil, epoxidized marine oils, epoxidized microorganism oils, vernonia oil, epoxidized methyl soyate, epoxidized methyl oleate, epoxidized methyl linolinate, epoxidized methyl linoleate, vernolic acid, or combinations thereof. By epoxidized marine oil, we mean triglycerides derived from the marine organisms in which at least some of the mono-, di-, and poly-unsaturated fatty acid portions have been transformed to epoxy groups. By microorganism oil, we mean triglycerides derived from the microorganisms in which at least some of the mono-, di-, and poly-unsaturated fatty acid portions have been transformed to epoxy groups.

In some embodiments, the organic compound is an amine, a phosphine, a guanidine derivative, or an onium compound.

In some embodiments, the organic compound is an amine wherein the amine comprises 2,4,6-Tris dimethylaminomethyl phenol, 2-Dimethylaminoethanol, N-Methyldiethanolamine, 3-Dimethylamino-1-propanol, 3-(Dimethylamino)-1,2-propanediol, 2-(Diethylamino)ethanol, 2-Dimethylamino-2-methylpropanol, 4-(Dimethylamino)-1-butanol, N-Ethyldiethanolamine, Triethanolamine, 3-Diethylamino-1-propanol, 2-{[2-(Dimethylamino)ethyl]methylamino}ethanol, 4-Diethylamino-2-butyn-1-ol, Tropine, 2-(Diisopropylamino)ethanol, 2-(Methylphenylamino)ethanol, 3-(Dimethylamino)benzyl alcohol, N-Phenyldiethanolamine, 2-(N-Ethyl-N-m-toluidino)ethanol, Methylphenylimino)diethanol, 3-(Dibenzylamino)-1-propanol, or combinations thereof.

In some embodiments, the organic compound is phosphine wherein the phosphine comprises (4-hydroxyphenyl)diphenylphosphine, tris(hydroxymethyl)phosphine.

In some embodiments, the organic compound is a guanidine compound.

In some embodiments, the organic compound is an onium compound and wherein the onium compound comprises an ammonium compound, an oxonium compound, a fluoronium compound, a phosphonium compound, a sulfonium compound, a chloronium compound, an arsonium compound, a selenonium compound, a boronium compound, a stilbonium compound, a telluronium compound, an iodonium compound, or bismuthonium compound. Examples of onium compounds include, but are not limited to, quaternary ammonium compounds including choline, candicine, and edrophonium, phosphonium compounds including tetrahydroxymethylphosphonium chloride, and sulfonium compounds including tris-(2-hydroxyethyl)-sulfonium chloride.

In some embodiments, wherein the reaction takes place in the presence of a catalyst.

In some embodiments, the catalyst comprises copper (II) tetrafluoroborate, cobalt (II) tetrafluoroborate, iron (II) tetrafluoroborate, zinc (II) tetrafluoroborate, nickel (II) tetrafluoroborate, and combinations thereof.

In some embodiments, the reaction takes place in the presence of a solvent.

In some embodiments, the solvent comprises acetone, methyl ethyl ketone, toluene, xylene, and combinations thereof.

In some embodiments, the cationic functional group is neutralized using carbon dioxide or a carboxylic acid or the cationic functional group is ion exchanged with a carboxylic acid.

In some embodiments, the cationic functional group is neutralized using a carboxylic acid comprising acetic acid, formic acid, proprionic acid, butyric acid, malic acid, lactic acid, citric acid, and combinations thereof; or the cationic functional group is ion exchanged using a carboxylic acid comprising acetic acid, formic acid, proprionic acid, butyric acid, malic acid, lactic acid, citric acid, or combinations thereof. The use of an organic acid to neutralize the cationic functional group or ion exchange the cationic functional group may reduce the aquatic toxicity compared to using mineral acids such as hydrochloric, hydrobromic, hydroiodic, sulfuric, hydrofluoric, and/or phosphoric acids.

In some embodiments, at least 70% of the cationic functional groups are neutralized or ion exchanged.

In some embodiments, the cationic functional group is neutralized and the hydrophilic to lipophilic balance is in the range of 4 to 40.

In another embodiment, the method of making a cationic surfactant comprises reacting a lipophilic bio-based material having at least one epoxy functional group with a hydrophilic organic compound having at least one cationic functional group and at least one hydroxyl functional group to form a reaction product containing an ether linkage connecting the lipophilic bio-based material to the hydrophilic organic compound, wherein the organic compound comprises an amine, a phosphine, a guanidine derivative, or an onium compound; and either: neutralizing the cationic functional group to form the surfactant, wherein at least 70% of the cationic functional groups are neutralized; or ion exchanging the counter ion in the cationic functional group with the counter ion in an acid, wherein at least 70% of the cationic functional groups are ion exchanged.

In some embodiments, the lipophilic bio-based material having at least one epoxy functional group comprises epoxidized soybean oil, epoxidized canola oil, epoxidized linseed oil, epoxidized high oleic soybean oil, epoxidized olive oil, epoxidized peanut oil, epoxidized palm oil, epoxidized hemp oil, epoxidized algal oil, epoxidized marine oils epoxidized microorganism oils, vernonia oil, epoxidized methyl soyate, epoxidized methyl oleate, epoxidized methyl linolinate, epoxidized methyl linoleate, vernolic acid, and combinations thereof.

In some embodiments, the organic compound is an amine comprising 2,4,6-Tris dimethylaminomethyl phenol, 2-Dimethylaminoethanol, N-Methyldiethanolamine, 3-Dimethylamino-1-propanol, 3-(Dimethylamino)-1,2-propanediol, 2-(Diethylamino)ethanol, 2-Dimethylamino-2-methylpropanol, 4-(Dimethylamino)-1-butanol, N-Ethyldiethanolamine, Triethanolamine, 3-Diethylamino-1-propanol, 2-{[2-(Dimethylamino)ethyl]methylamino}ethanol, 4-Diethylamino-2-butyn-1-ol, Tropine, 2-(Diisopropylamino)ethanol, 2-(Methylphenylamino)ethanol, 3-(Dimethylamino)benzyl alcohol, N-Phenyldiethanolamine, 2-(N-Ethyl-N-m-toluidino)ethanol, Methylphenylimino)diethanol, 3-(Dibenzylamino)-1-propanol, and combinations thereof.

In some embodiments, a hydrophilic to lipophilic balance is in a range of 4 to 40. Another aspect of the invention is a cationic surfactant. In one embodiment, the cationic surfactant comprises a reaction product of a lipophilic bio-based material having at least one epoxy functional group and a hydrophilic organic compound having at least one cationic functional group and at least one hydroxyl functional group, wherein the lipophilic bio-based material is connected to the organic compound by an ether linkage.

In some embodiments, at least a portion of the cationic functional groups are neutralized or ion exchanged.

In some embodiments, the lipophilic bio-based material having at least one epoxy functional group comprises epoxidized soybean oil, epoxidized canola oil, epoxidized linseed oil, epoxidized high oleic soybean oil, epoxidized olive oil, epoxidized peanut oil, epoxidized palm oil, epoxidized hemp oil, epoxidized algal oil, epoxidized marine oils epoxidized microorganism oils, vernonia oil, epoxidized methyl soyate, epoxidized methyl oleate, epoxidized methyl linolinate, epoxidized methyl linoleate, vernolic acid and combinations thereof.

In some embodiments, the organic compound is an amine, a phosphine, a guanidine derivative, or an onium compound.

In some embodiments, the organic compound comprises an amine having at least one hydroxyl functional group and wherein the amine comprises of 2,4,6-Tris dimethylaminomethyl phenol, 2-Dimethylaminoethanol, N-Methyldiethanolamine, 3-Dimethylamino-1-propanol, 3-(Dimethylamino)-1,2-propanediol, 2-(Diethylamino)ethanol, 2-Dimethylamino-2-methylpropanol, 4-(Dimethylamino)-1-butanol, N-Ethyldiethanolamine, Triethanolamine, 3-Diethylamino-1-propanol, 2-{[2-(Dimethylamino)ethyl]methylamino}ethanol, 4-Diethylamino-2-butyn-1-ol, Tropine, 2-(Diisopropylamino)ethanol, 2-(Methylphenylamino)ethanol, 3-(Dimethylamino)benzyl alcohol, N-Phenyldiethanolamine, 2-(N-Ethyl-N-m-toluidino)ethanol, Methylphenylimino)diethanol, 3-(Dibenzylamino)-1-propanol, and combinations thereof.

In some embodiments, the organic compound is phosphine wherein the phosphine comprises (4-hydroxyphenyl)diphenylphosphine, tris(hydroxymethyl)phosphine.

In some embodiments, the organic compound is a guanidine compound.

In some embodiments, the organic compound is an onium compound and wherein the onium compound comprises an ammonium compound, an oxonium compound, a fluoronium compound, a phosphonium compound, a sulfonium compound, a chloronium compound, an arsonium compound, a selenonium compound, a boronium compound, a stilbonium compound, a telluronium compound, an iodonium compound, or bismuthonium compound. Examples of onium compounds include, but are not limited to, quaternary ammonium compounds including choline, candicine, and edrophonium, phosphonium compounds including tetrahydroxymethylphosphonium chloride, and sulfonium compounds including tris-(2-hydroxyethyl)-sulfonium chloride.

In some embodiments, the cationic functional group is neutralized using carbon dioxide or a carboxylic acid, or the cationic functional group is ion exchanged with a carboxylic acid.

In some embodiments, the cationic functional group is neutralized or the cationic group is ion exchanged using a carboxylic acid comprising acetic acid, formic acid, proprionic acid, butyric acid, malic acid, lactic acid, citric acid, and combinations thereof.

In some embodiments, the cationic functional groups are neutralized or ion exchanged with a carboxylic acid comprising acetic acid, formic acid, proprionic acid, butyric acid, malic acid, lactic acid, citric acid, or combinations thereof.

In some embodiments, at least 70% of the amine groups are neutralized or ion exchanged.

In some embodiments, wherein the cationic functional groups are neutralized and wherein a hydrophilic to lipophilic balance is in a range of 4 to 40.

The invention is further illustrated with the following examples.

EXAMPLES

Example 1

60.08 g epoxidized soy bean oil (ESBO), and 55.11 g 2,4,6-tris(dimethylaminomethyl) phenol were charged in a 250 mL 3-neck roundbottom flask fitted with a water cooled condenser, overhead stirrer, dry/inert argon gas purge, and a thermocouple-heating mantle-temperature controller network. The mixture was heated to 60° C. for 24 hours while stirring under gas purge. The mixture was cooled to room temperature, and bottled as an oily solid. 50 grams of glacial acetic acid (99%) was added dropwise to 20 grams of the above product. The mixture was vacuum treated at 29 mm Hg vacuum at 100° C. for 4 hours to drive off excess acetic acid and any water to produce the cationic surfactant.

Example 2

213.02 g of epoxidized soybean oil methyl ester and 241.02 g of 2,4,6-tris(dimethylaminomethyl) phenol were charged in a 500 mL 3-neck roundbottom flask fitted with a water cooled condenser, overhead stirrer, dry/inert argon gas purge, and a thermocouple-heating mantle-temperature controller network. The mixture was heated to 120° C. and maintained for 24 hours to obtain a uniform solid. The product was cooled to room temperature. 161.88 g of acetic acid were mixed in very slowly, and the mixture was mixed overnight to yield a amber-clear solution having a pH of 5-6.

Example 3

In the first step, the epoxy functional bio-based material namely octadecyl glycidyl ether was formed by reacting 60.30 g 1-octadecanol, 47.50 g epichlorohydrin, 18.10 g sodium hydroxide, and 0.54 g tetrabutyl ammonium hydroxide (TBAB) in a 250 mL 3-neck roundbottom flask fitted with a water cooled condenser, overhead stirrer, dry/inert argon gas purge, and a thermocouple-heating mantle-temperature controller network. The mixture was heated at 60° C. overnight. The next day, the mixture was cooled to room temperature to obtain a light white colored waxy solid.

49.99 g octadecyl glycidyl ether obtained was mixed with 40.63 g 2,4,6-tris(dimethylaminomethyl) phenol in a 250 mL 3-neck roundbottom flask fitted with a water cooled condenser, overhead stirrer, dry/inert argon gas purge, and a thermocouple-heating mantle-temperature controller network. The mixture was heated to 60° C. overnight to obtain a uniform solid. It was slowly heated to 60° C. to melt the solid, and a bubbler was inserted. The temperature was increased to 120° C., and that temperature was maintained overnight. The reactor was cooled to 60° C., and 90.01 g of ethanol was added. 22.07 g glacial acetic acid was slowly charged to bring the pH down to 6 to obtain the cationic surfactant.

Testing Methodology

The cationic surfactants were tested for emulsion and rock-fluid behavior with dolomitic reservoir rocks and oil sampled from a producing oil well in Morrow County, Ohio.

Interfacial Tension (IFT) was measured using the Du Nuoy method which uses a platinum ring that contacts the immiscible fluids and measures changes in force as it passes through their interface. Tension at the interface is then calculated using the recorded force and the diameter of the ring. For oil-water IFT, the ring is originally placed in the aqueous phase, the liquid level is lowered, and the position where the ring separates off from the aqueous phase and completely moves into the oil phase is measured. The experimental setup comprises a Thermo Cahn 300 series surface/interfacial tension measuring device equipped with a platinum-iridium ring and a glass measurement cell which is approximately 1.5 inch in diameter. The device was calibrated before measurements by measuring the air-water IFT which is 72 dynes/cm at standard atmospheric conditions. All the IFT measurements were conducted at standard atmospheric conditions. Surfactant concentrations varying from 0.5 gallons per thousand gallons (gpt) to 4 gpt were used to obtain an IFT vs. concentration profile.

Wettability was characterized by measuring the contact angle of water on aged reservoir rock in the presence of an ambient decane phase used to mimic crude oil. Sessile drop technique was used to measure the contact angle. In this method, a water drop is placed on the rock surface in the presence of a less dense ambient phase such as air/oil. Devices that use this methodology are often equipped with a goniometer that captures a snapshot/video of the drop on rock surface, which is later processed using a drop shape analyzer (DSA) software to yield contact angle. AST Products Inc.'s Video Contact Angle (VCA) Optima was the instrument used for this study. The device interfaced with VCA OptimaXE image processing software to capture and analyze rock-fluid snapshots. All the measurements were performed at room temperature and pressure.

Spontaneous imbibition was conducted using a modified Amott cell which consisted of a base and top clamped together by a pair of aluminum rings and three aluminum screws. The base holds the core sample while the base and top parts are filled with testing/imbibing fluid. The top also has a graduated capillary column which is meant for collecting and measuring the oil recovered from the experiment. The top of the cell is usually plugged with a stopper or covered in parafilm to prevent loss of vapors. Prior to being immersed in imbibition fluids, the aged core samples were removed from oil and excess oil is wiped off to measure the weight of the core after saturation. This is compared with the weight of the core before saturation and volumetric calculation are carried out to quantify changes in saturation. Once the post aging weight of samples for saturation calculations were noted, the cores were placed in the modified Amott cells that were subsequently filled with surfactant solutions. Surfactant solutions were prepared at 3 gpt concentration. All the experiments were conducted at reservoir temperature. Oil recovered from the experiments was periodically monitored and converted to a normalized recovery factor based on the oil originally in place (OOIP). More information on the construction of the Amott cells and volumetric calculations of the aging process and recovery factors can be found in Valluri et al (2017).

The toxicity of cationic surfactants disclosed in Example 1 was assessed using BG1LUC assay as per the previously reported procedure. (References: OECD Guideline for the Testing of Chemicals: BG1Luc Estrogen Receptor Transactivation Test Method for Identifying Estrogen Receptor Agonists and Antagonists, OECD Guidelines for the Testing of Chemicals, Section 4, OECD Publishing, Paris, https://doi.org/10.1787/9789264185395-en, and http://ntp.niehs.nih.gov/ntp/about_ntp/sacatm/2012/september/d_draft_oecdtg457bg1luc_508.pdf; and G. Bittner, M. Denison, C. Yang, M. Stoner and G. He, Environmental Health 2014, 13 103). They were also tested for aquatic toxicity according to Method 2007 using Mysidopsis Bahia.

Results and Conclusions

Surfactants obtained from Example 1 and Example 3 were tested. Both versions reduced the IFT with increasing aqueous concentration which is typical of most surfactants used for improving oil recovery. However, the cationic surfactant obtained from Example 3 resulted in lower IFT than the cationic surfactant obtained from Example 1 at low concentrations of 1 gpt and 2 gpt. Although not wishing to be bound by theory, we believe this is because the cationic surfactant obtained from Example 1 was a triglyceride-based molecule and was subject to steric hindrance which impeded its activity at the oil-water interface and micelle formation. As a result, the cationic surfactant obtained from Example 3 was chosen for the oil recovery test.

Prior to the contact angle measurements, the reservoir rock chips were aged to restore their native state. The initial contact angle without any surfactant was found to be 132.6° which implies the original state of the reservoir was oil-wet. Increasing the concentration of the soy-based surfactant in the aqueous phase resulted in the reduction of contact angle, implying that the adhesive forces between water and rock improved, i.e., water-wetness increased. At a typical oilfield concentration of 2 gpt of the surfactant, the contact angle was 77.4°, implying mixed wetness tending towards water-wet.

The soy-based surfactant outperformed commercial anionic and cationic surfactants in oil recovery tests, recovering 35% of the oil originally in place (OOIP) inside the rock, while the commercial cationic and anionic surfactants recovered 27% and 18% of OOIP, respectively.

Toxicity testing of the cationic surfactant described in Example 1 showed no estrogenic or anti-estrogenic activity, indicating the cationic surfactants obtained from this invention are non-toxic. Aquatic toxicity testing of the surfactant described in Example 2 showed a 96-hour LC50 of 46 mg/L, compared to 0.2 mg/L for CTAB (cetyl trimethyl ammonium bromide), a common cationic surfactant in the oil and gas industry.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method of making a cationic surfactant comprising:
   reacting a lipophilic bio-based material having at least one epoxy functional group with a hydrophilic organic compound having at least one cationic functional group and at least one hydroxyl functional group in the presence of a catalyst comprising a salt of tetrafluoroborate to form a reaction product containing an ether linkage connecting the lipophilic bio-based material to the organic compound;
   wherein the lipophilic material is selected from epoxidized soybean oil, epoxidized canola oil, epoxidized linseed oil, epoxidized high oleic soybean oil, epoxidized olive oil, epoxidized peanut oil, epoxidized palm oil, epoxidized hemp oil, epoxidized algal oil, epoxidized marine oils epoxidized microorganism oils, vernonia oil, epoxidized methyl soyate, epoxidized methyl oleate, epoxidized methyl linolinate, epoxidized methyl linoleate, vernolic acid, or combinations thereof; and
   wherein the organic compound comprises an amine, a phosphine, a guanidine derivative, or an onium compound.

2. The method of claim 1 further comprising:
   neutralizing the cationic functional group in the reaction product; or
   ion exchanging the counter ion in the cationic functional group.

3. The method of claim 1 wherein the organic compound is the amine and wherein the amine comprises 2,4,6-Tris dimethylaminomethyl phenol, 2-Dimethylaminoethanol, N-Methyldiethanolamine, 3-Dimethylamino-1-propanol, 3-(Dimethylamino)-1,2-propanediol, 2-(Diethylamino)ethanol, 2-Dimethylamino-2-methylpropanol, 4-(Dimethylamino)-1-butanol, N-Ethyldiethanolamine, Triethanolamine, 3-Diethylamino-1-propanol, 2-{[2-(Dimethylamino)ethyl]methylamino}ethanol, 4-Diethylamino-2-butyn-1-ol, Tropine, 2-(Diisopropylamino)ethanol, 2-(Methylphenylamino)ethanol, 3-(Dimethylamino)benzyl alcohol, N-Phenyldiethanolamine, 2-(N-Ethyl-N-m-toluidino)ethanol, 2,2'-(4-Methylphenylimino)diethanol, 3-(Dibenzylamino)-1-propanol, or combinations thereof.

4. The method of claim 1 wherein the organic compound is the phosphine and wherein the phosphine comprises (4-hydroxyphenyl)diphenylphosphine, tris(hydroxymethyl) phosphine.

5. The method of claim 1 wherein the organic compound is the guanidine derivative.

6. The method of claim 1 wherein the organic compound is the onium compound and wherein the onium compound comprises an ammonium compound, an oxonium compound, a fluoronium compound, a phosphonium compound, a sulfonium compound, a chloronium compound, an arsonium compound, a selenonium compound, a boronium compound, a stilbonium compound, a telluronium compound, an iodonium compound, or bismuthonium compound, or combinations thereof.

7. The method of claim 1 wherein the reaction takes place in the presence of a solvent.

8. The method of claim 1 wherein the cationic functional group is neutralized using carbon dioxide or a carboxylic acid or the cationic functional group is ion exchanged with a carboxylic acid.

9. The method of claim 1 wherein the cationic functional group is neutralized using a carboxylic acid comprising acetic acid, formic acid, proprionic acid, butyric acid, malic acid, lactic acid, citric acid, or combinations thereof; or wherein the cationic functional group is ion exchanged using a carboxylic acid comprising acetic acid, formic acid, proprionic acid, butyric acid, malic acid, lactic acid, citric acid, or combinations thereof.

10. The method of claim 1 wherein at least 70 mol % of the cationic functional groups are neutralized or ion exchanged.

11. The method of claim 1 wherein the cationic functional group is neutralized and wherein a hydrophilic to lipophilic balance is in a range of 4 to 40.

* * * * *